United States Patent
Chen et al.

(10) Patent No.: US 7,739,829 B2
(45) Date of Patent: Jun. 22, 2010

(54) KILLING INSECT PESTS INSIDE WOOD BY VACUUM DEHYDRATION

(75) Inventors: Zhangjing Chen, Blacksburg, VA (US); Marshall S. White, Blacksburg, VA (US); William H. Robinson, Christiansburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 11/574,551

(22) PCT Filed: Jul. 11, 2005

(86) PCT No.: PCT/US2005/024520

§ 371 (c)(1),
(2), (4) Date: Sep. 11, 2007

(87) PCT Pub. No.: WO2006/028572

PCT Pub. Date: Mar. 16, 2006

(65) Prior Publication Data

US 2008/0127548 A1   Jun. 5, 2008

(51) Int. Cl.
*A01M 1/20* (2006.01)
*F26B 5/04* (2006.01)
*F26B 3/20* (2006.01)

(52) U.S. Cl. .................. 43/132.1; 43/124; 34/92; 34/299; 422/33

(58) Field of Classification Search ........... 43/132.1, 43/124; 34/92, 396, 413, 299; 118/50, 50.1; 422/33, 38; 427/294, 296, 297
See application file for complete search history.

(56) References Cited

U.S. PATENT DOCUMENTS

| | | | | | |
|---|---|---|---|---|---|
| 1,355,476 | A | * | 10/1920 | Hering | 43/124 |
| 1,672,326 | A | * | 6/1928 | Kobiolke | 34/416 |
| 1,817,531 | A | * | 8/1931 | Spanel | 422/33 |
| 2,012,975 | A | * | 9/1935 | Schmittutz | 427/291 |
| 2,040,600 | A | * | 5/1936 | Davis | 43/138 |
| 2,073,634 | A | * | 3/1937 | Hodnefield et al. | 424/126 |
| 2,838,424 | A | * | 6/1958 | Depew et al. | 427/297 |
| 3,094,431 | A | * | 6/1963 | Goldstein et al. | 427/254 |

(Continued)

FOREIGN PATENT DOCUMENTS

DE   202005006510 U1 * 11/2005

(Continued)

*Primary Examiner*—Darren W Ark
(74) *Attorney, Agent, or Firm*—Whitham Curtis Christofferson & Cook, PC

(57) ABSTRACT

Insect pests can be transported around the world in wooden shipping containers. To prevent the spread of wood-borne insect pests, it is necessary to kill insects within the wood. The wood is placed in a vacuum container having a flexible wall. The flexible wall presses against the wood and enables the wood to be heated by conduction. The wood and flexible wall can to be heated by contact with ambient or heated air, for example. Desiccant or dry air can be used to increase the rate of dehydration. Insects in the wood are typically killed after losing 25-50% of their body weight by dehydration. This technique will kill beetle larvae, nematodes and other invasive and destructive insects that live inside solid wood, and is particularly applicable for rendering wood acceptable for use in pallets and other containers shipped internationally.

8 Claims, 2 Drawing Sheets

U.S. PATENT DOCUMENTS

| | | | | |
|---|---|---|---|---|
| 3,199,211 | A * | 8/1965 | Bescher | 34/342 |
| 3,309,778 | A * | 3/1967 | Erickson | 34/284 |
| 3,342,629 | A * | 9/1967 | Martin | 422/40 |
| 3,394,462 | A * | 7/1968 | Bondurant | 34/339 |
| 3,466,756 | A * | 9/1969 | Tooby | 34/299 |
| 3,521,373 | A * | 7/1970 | Pagnozzi | 34/92 |
| 3,571,943 | A * | 3/1971 | Sipple | 34/415 |
| 3,818,601 | A * | 6/1974 | Cooper et al. | 34/396 |
| 3,894,345 | A * | 7/1975 | Zeltmann | 34/93 |
| 3,914,874 | A * | 10/1975 | Bruce | 34/92 |
| 3,939,573 | A * | 2/1976 | Berti | 34/496 |
| 3,968,276 | A * | 7/1976 | Allen | 427/297 |
| 4,058,906 | A * | 11/1977 | Pagnozzi | 34/92 |
| 4,121,350 | A * | 10/1978 | Buchholz | 34/92 |
| 4,129,091 | A * | 12/1978 | France et al. | 118/50 |
| 4,156,043 | A * | 5/1979 | France et al. | 427/297 |
| 4,187,346 | A * | 2/1980 | Jarrett | 427/297 |
| 4,197,657 | A * | 4/1980 | Leino et al. | 34/92 |
| 4,198,763 | A * | 4/1980 | Kurihara | 34/92 |
| 4,343,095 | A * | 8/1982 | Rosen et al. | 34/92 |
| 4,466,198 | A * | 8/1984 | Doll | 34/92 |
| 4,467,532 | A * | 8/1984 | Drake | 34/92 |
| 4,620,373 | A * | 11/1986 | Laskowski et al. | 34/92 |
| 4,734,995 | A * | 4/1988 | Pagnozzi et al. | 34/92 |
| 4,817,329 | A * | 4/1989 | Forbes | 43/132.1 |
| 4,961,283 | A * | 10/1990 | Forbes | 43/132.1 |
| 5,103,575 | A * | 4/1992 | Yokoo et al. | 34/255 |
| 5,143,748 | A * | 9/1992 | Ishikawa et al. | 427/297 |
| 5,199,186 | A * | 4/1993 | Rice et al. | 34/92 |
| 5,203,108 | A * | 4/1993 | Washburn, Jr. | 43/132.1 |
| 5,282,322 | A * | 2/1994 | Kasuya | 34/92 |
| 5,365,692 | A * | 11/1994 | Gustafson | 43/132.1 |
| 5,378,086 | A * | 1/1995 | Campbell et al. | 43/124 |
| 5,392,530 | A * | 2/1995 | Izumi | 34/92 |
| 5,395,656 | A * | 3/1995 | Liang | 427/297 |
| 5,512,098 | A * | 4/1996 | French et al. | 118/50 |
| 5,687,490 | A * | 11/1997 | Harrison | 34/92 |
| 5,783,258 | A * | 7/1998 | Garapick | 427/298 |
| 5,792,419 | A * | 8/1998 | Williamson et al. | 43/124 |
| 5,852,879 | A * | 12/1998 | Schumaier | 34/80 |
| 5,852,880 | A * | 12/1998 | Harrison | 34/92 |
| 5,970,624 | A * | 10/1999 | Moriya | 34/396 |
| 6,014,819 | A * | 1/2000 | Elder | 34/396 |
| RE36,728 | E * | 6/2000 | Ishii | 34/396 |
| 6,094,835 | A * | 8/2000 | Cromer | 34/80 |
| 6,151,795 | A * | 11/2000 | Hoffman et al. | 34/92 |
| 6,327,812 | B1 * | 12/2001 | Hedman et al. | 43/132.1 |
| 6,447,737 | B1 * | 9/2002 | Williamson et al. | 43/124 |
| 6,586,054 | B2 * | 7/2003 | Walsh | 427/294 |
| 6,588,140 | B1 * | 7/2003 | Johnson et al. | 43/132.1 |
| 6,612,067 | B2 * | 9/2003 | Topp | 43/124 |
| 6,634,118 | B2 * | 10/2003 | Chen et al. | 34/92 |
| 6,751,887 | B2 * | 6/2004 | Hanhi | 34/250 |
| 6,865,821 | B2 * | 3/2005 | Merschat | 34/92 |
| 2002/0178608 | A1* | 12/2002 | Leonovs | 34/418 |
| 2003/0115768 | A1* | 6/2003 | Hoffman | 34/92 |
| 2005/0108920 | A1* | 5/2005 | Takenoshita et al. | 43/132.1 |
| 2007/0101606 | A1* | 5/2007 | Philipp et al. | 34/282 |

FOREIGN PATENT DOCUMENTS

| | | |
|---|---|---|
| DE | 102005009972 A1 * | 9/2006 |
| JP | 02081603 A * | 3/1990 |
| JP | 07031349 A * | 2/1995 |
| JP | 07035475 A * | 2/1995 |
| JP | 11023150 A * | 1/1999 |
| JP | 2002079504 A * | 3/2002 |
| JP | 2004268494 A * | 9/2004 |
| WO | PCT/ZA01/00188 | 12/2001 |
| WO | WO 0246670 A1 * | 6/2002 |
| WO | WO 2006077073 A1 * | 7/2006 |

* cited by examiner

KILLING INSECT PESTS INSIDE WOOD BY VACUUM DEHYDRATION

Development of the present invention was supported in part by grant numbers 03-0301-08 and 04-1108-12 by the Limestone Bluffs RC&D of the US Forest Service. The Government has certain rights in the invention.

FIELD OF THE INVENTION

The present invention relates generally to methods for killing pest insects inside wood. Particularly, the present invention relates to methods for killing insects inside wood using a combination of vacuum, heat and dehydration.

BACKGROUND OF THE INVENTION

Wooden pallets, boxes and containers are commonly used for shipping products and material. One problem with using wooden shipping containers is that the wood can contain and thereby facilitate the spread of insect pests such as wood boring beetles. This is particularly a problem for international shipping because infested wood containers can introduce invasive and destructive species to new areas. Destructive species can cause billions of dollars of damage to forests and wood products industries and create long-lasting pest control problems. There is therefore an urgent need for methods to reliably kill pests within wood materials used for shipping containers.

To prevent the spread of destructive insect pests in wood and other materials, the United States and its trading partners have adopted regulations known as the International Standard for Phytosanitary Measures (ISPM). Presently, these regulations require heat treatment of wood shipping materials at least 56 degrees Celsius for 30 minutes, or fumigation in methyl bromide. Though effective for killing pests, these methods for wood treatment are problematic. Heat treatment is energy intensive and therefore expensive. Methyl bromide is toxic, is damaging to the Earth's ozone layer and can affect the appearance and properties of the wood. Methyl bromide can also render the wood unsuitable for certain uses.

Another problem with both heat treatment and fumigation is that the wood must be "stickered" (separated with spacers to provide air gaps) before treatment so that heat and chemicals can penetrate the lumber stack. Stickering a pile of lumber is time consuming and labor intensive because the entire stack must be manipulated and interleaved with air spacers. Eliminating the stickering step would significantly reduce the time and cost of wood treatment.

Due to the importance of eliminating invasive insect pests, and the problems inherent in conventional methods for wood pest control, there is an urgent need for new methods for controlling wood pests. It would be particularly beneficial to provide a method for controlling wood insect pests that is environmentally benign, inexpensive and energy efficient. Additionally, a method that does not require stickering would provide significant cost advantages.

SUMMARY OF THE INVENTION

The present invention provides methods for reliably killing insect pests in wood. In the present invention, infested wood is disposed inside a vacuum container having a flexible wall. The vacuum container is evacuated and the flexible wall collapses against the wood due to atmospheric pressure. Then, the wood is heated by conduction through the flexible wall. The heat can be provided by air at ambient temperature, or a heat source having a temperature above ambient (e.g. a hot water bath or electric blanket). The wood is evacuated and heated until the insects are killed by dehydration.

The wood can be in thermal contact with a heat source having a temperature in the range of 15-30° C., or 30-55° C. The vacuum container, wood and insects can be heated by exposing the vacuum container to sunlight, for example.

Preferably, the wood remains in the vacuum container until the insects lose at least 20% or 30% of their weight by dehydration.

Preferably, the wood has an initial moisture content (by weight) of less than 50%, and more preferably less than 25%. A low initial moisture content in the wood results in faster and more reliable destruction of the insects. The amount of time that the wood is exposed to vacuum can be selected based on the initial moisture content of the wood.

Additionally, desiccant can be disposed within the vacuum container to increase the rate of dehydration. Also, dry gas can be flowed into the vacuum container to increase the rate of dehydration.

The present invention also includes an embodiment in which insects are killed by exposing the wood to a combination of vacuum and desiccant material.

DETAILED DESCRIPTION OF THE INVENTION

The present invention provides novel methods for killing insect pests in wood. In the present invention, wood with insect pests is disposed in a collapsible, vacuum tight container having a flexible wall. The container is evacuated with a vacuum pump, and the walls of the container press against the wood due to atmospheric pressure. Heat is applied to the container so that the wood is heated by conduction. The applied heat maintains the temperature of the wood even as water is evaporated. The heat tends to greatly increase the rate of dehydration of the insects within the wood. Eventually, dehydration of the insects kills the insects. Typically, dehydration kills the insects after they have lost about 25-50% or more of their body weight. Optionally, desiccant is added to the container to further increase the rate of dehydration. Dry air can also be flowed into the container to increase the rate of dehydration. The method of the present invention is energy efficient and nonpolluting, and is particularly well suited for rendering wood safe to use for containers for international shipping. The method of the present invention will kill a wide range of wood boring beetles, beetle larvae, nematodes, worms, and the like.

Figure 1:
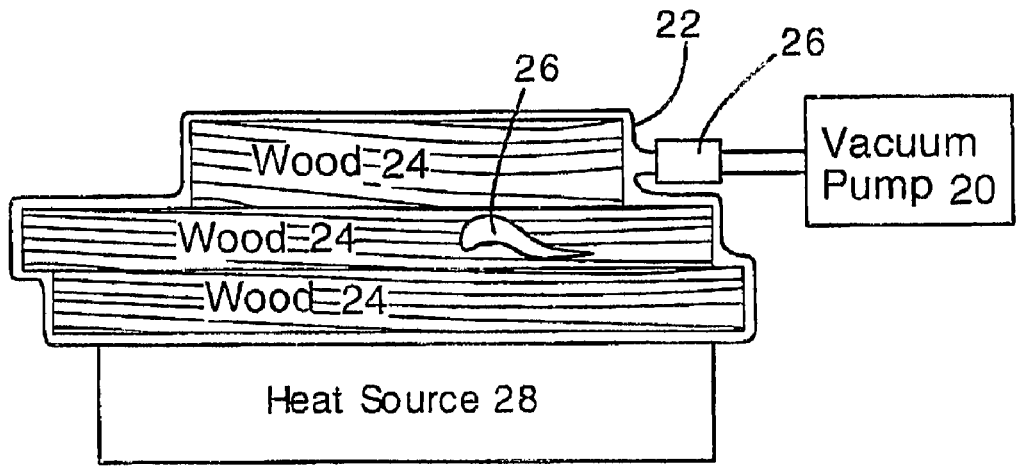
FIG. 1 shows an apparatus for killing insect pests inside wood by vacuum dehydration.

FIG. 1 shows an apparatus for performing the method of the present invention. The apparatus comprises a vacuum pump 20 connected to a flexible vacuum container 22. Wood 24 containing undesired wood pests 26 is disposed within the flexible vacuum container 22. The vacuum pump 20 and container 22 can be connected by a re-attachable connector 26.

The wood pests 26 may be beetle larvae, mature beetles, nematodes, worms, moths, or other kinds of insects, spiders or other small animals. Specific pest organisms of concern to users of wood pallets and containers and that can be killed according to the present invention include the asian longhorn beetle (*anoplophora glabripennis*), ribbed pine borer (*stenocorus lineatus*), sawyer beetle (*monochamus carolinensis*), pinewood nematode (*bursaphelenchus xylophilus*), emerald ash borer, and the old house borer beetle (*hylotrupes bajulus*). Other species can also be killed according to the present method.

The vacuum pump is preferably a mechanical roughing pump. Typically, the pump can produce a vacuum with a pressure less than 200, 100, 50 or 20 Torr. The pump can be powered by an electric motor, or by a gasoline engine, for example. A device for absorbing or removing moisture (e.g. a condenser) may be included in the path between the vacuum container 22 and the vacuum pump 20 to protect the pump from damage caused by moisture exposure.

The flexible vacuum container can be made of many different fluid-impervious materials such as polyvinyl chloride (PVC), rubber, Mylar (polyester film), and the like. The bag can be reinforced with fibrous material or fabric such as nylon or other fibers. The container 22 preferably has a re-sealable opening (not shown) for removing wood from and placing wood within the container. The container 22 may comprise a bag having only flexible walls.

Preferably, the container 22 is disposed to receive heat energy from a heat source 28. The heat source maintains the wood at ambient temperature or above by heat conduction through the walls of the container 22. The heat source 28 can comprise a hot water bath, a hot bath of any other of flowable material (e.g. sand, oil, or air), a warm room, sunlight, an electric heater blanket, or hot circulating air heated by a burner (e.g. a propane or natural gas burner). The heat source 28 may have a temperature in the range of about 20-60 degrees Celsius, for example). The heat source may simply be air at ambient temperature (e.g. 10-30 degrees Celsius). For example, the container 22 and wood may be located in a warehouse or outdoors at ambient temperature.

In operation, wood 24 is disposed within the container 22. The wood 24 may comprise a stack of many different shapes and sizes of lumber. The stack of wood in the container can be very large and comprise hundreds or thousands of pounds of wood. The vacuum pump 20 evacuates the container 22. The walls of the container 22 collapse against the wood 24. Therefore, heat from outside the container 22 conducts through the flexible container walls, and into the wood and insects. Moisture from the insects 26 evaporates and is exhausted by the vacuum pump 20. Heat conduction through the container maintains the wood and insects 26 at a temperature necessary for continued evaporation of moisture at a reasonable and useful rate.

The pressure within the container 22 can be maintained at less than about 100 Torr. Typically, the pressure in the container will be maintained at about 10-40 Torr. In this pressure range, insects are rapidly dehydrated, particularly when the temperature of the wood and insects is maintained by heat conduction through the container walls. The rapid dehydration kills the insects 26; typically insects die when they have lost about 30 or 40% of their body weight by dehydration. Most beetle larvae and nematodes die in less than 24 hours when exposed to a vacuum of 20 mmHg and maintained at temperatures in the range of about 20-25° Celsius, provided that the insects do not have access to water (e.g. from moisture in the wood).

It is important to note that, without the flexible container 22 of the present invention, it is difficult to sustain rapid dehydration of the insects 26. When insects 26 and wood 24 are disposed in a rigid container, as in the prior art, vacuum causes rapid reduction in temperature by evaporation, which tends to greatly reduce the rate of dehydration. A rigid container maintains a vacuum around the wood, which thermally insulates the wood and insects, thereby allowing the wood and insects to become much colder than the surrounding environment. Cold temperatures slow the rate of dehydration and allow insects to survive for extended periods (e.g. longer than 48 or 60 hours) in the vacuum. For this reason, the maintaining the temperature of the wood and insects (by contact between the wood and flexible wall of the vacuum container 22) greatly increases the rate of dehydration of the insects.

In experiments performed by the present inventors, larvae of beetles were inserted into holes drilled into wood samples. The holes were then sealed with tight-fitting wooden dowels. The wood samples were then placed in the vacuum container. The insects were periodically removed from the vacuum container, weighed to determine the percentage body weight loss from dehydration, and observed to determine if they were alive or dead. Since only periodic observation is possible with this method, the exact time of death, and therefore the exact body weight at the precise time of death, could not be determined.

The wood samples containing the insects were typically air dried before insects were inserted (e.g. to about 5-15% moisture content), though some wood samples were not dried. Some insects can obtain moisture from moist wood, which tends to protect the organism from dehydration and allow it to survive in the vacuum for longer duration.

Typically, it was observed that insects were killed by moisture loss of about 25-30% or more by weight. Moisture loss of less than 20% by weight was often not enough dehydration to reliably kill the insects. Most generally, in the present invention, the weight loss of the insects should be greater than 20% to assure the insects are killed. The weight loss can be in the range of 20-80% for example.

Below are listed some experimental results demonstrating the efficacy of the present invention. All the experiments were performed with a vacuum of 20 mmHg and at a temperature of 20 degrees Celsius. The vacuum container used was a PVC flexible container evacuated with a mechanical roughing pump. Typically the larvae had initial weights of about 225-400 milligrams.

TABLE 1

Experimental results with various larvae and wood types

| Species and quantity | Time (hours) | Initial moisture content (MC) of wood | Average and range of weight loss | Result |
|---|---|---|---|---|
| Ribbed pine borer larvae (9 organisms) | 90 hours | 9% MC | Average: 66.3% Range: 59-71.8% | 100% dead |
| Sawyer beetle larvae (7 organisms) | 90 hours | 9% MC | Average: 69.9% Range: 55-84% | 100% dead |
| Ribbed pine borer larvae (5 organisms) | 24 hours | 31% MC | Average: 51.9% Range: 46-55.4% | 100% dead |
| Ribbed pine borer larvae (4 organisms) | 24 hours | 9% MC | Average: 61.3% Range: 55.1-67.5% | 100% dead |
| Ribbed pine borer larvae | 12 hours | 42% MC | Average: 25.8% Range: 14.8-58% | 66% dead (10 of 18) |

TABLE 1-continued

Experimental results with various larvae and wood types

| Species and quantity | Time (hours) | Initial moisture content (MC) of wood | Average and range of weight loss | Result |
|---|---|---|---|---|
| (18 organisms) | | | | 10 Dead avg: 32% 8 Alive avg: 18.2% |

It is important to note that, in the experiments listed above, the wood moisture content was not significantly reduced by exposure to vacuum. Typically, the reduction in moisture content of the wood was about 1-3%. This is because in all the above-listed experiments the wood was maintained at ambient room temperature of about 20 degrees Celsius. In order to dry the wood by vacuum in a reasonable period of time, it is generally necessary to heat the wood above 30 degrees Celsius or higher. Insects dehydrate much more rapidly than wood at ambient temperatures (e.g. 15-30 degrees Celsius). Hence, when performed at ambient temperatures, the present method can be used to kill insects by dehydration without substantially affecting the moisture content of the wood. If it is desired to both reduce the wood moisture content, and kill the insects more rapidly, then the wood can be heated to temperatures in the range of 30-50 degrees Celsius, for example. As noted above, the wood is easily heated by conduction because it is in physical contact with the walls of the flexible vacuum container.

The inventors have determined that wood insects exposed to vacuum while inside wood are killed by dehydration, not by asphyxiation or lack of oxygen. This was proven by experiments in which insects inserted into wood with a high moisture content (e.g. 50-70%) could survive for several days in vacuum with little or no oxygen. In these experiments, the insects obtained moisture from the wood, and thereby avoided dehydration. For example, in the final experiment in the table above, the larvae were able to survive for 12 hours in wood having a moisture content of 42%, despite the almost complete lack of oxygen during this time.

In experiments performed by the present inventors, it has been found that the larvae of the old house borer beetle (*hylotrupes bajulus*) are particularly resistant to dehydration by vacuum. This is apparently because the old house borer beetle larvae have an exceptional ability to obtain moisture from wood during the vacuum dehydration process. Consequently, is old house borer beetle larvae are capable of surviving extended vacuum exposure in wood having a high moisture content (e.g. about 40 or 50% moisture). Also, old house borer beetle larvae are adapted for living in wood with low moisture content (e.g. less than 10%), and at high temperatures. Empirically, it has been determined that larvae of the old house borer beetle are perhaps the most resistant to vacuum dehydration of all the common wood infesting pests. Due to its importance as a pest species, and its resistance to vacuum dehydration and dehydration generally, the old house borer beetle larvae was used as a test species for the present invention in a series of experiments.

In experiments with old house borer beetle larvae, the time required for reliably killing the larvae was found to depend greatly on the initial moisture content of the wood. Below is a table summarizing the results of experiments with old house borer beetle larvae. All experiments were performed with a vacuum of about 20 mmHg and at a temperature of about 20 degrees Celsius. The wood and larvae were maintained at this temperature due to contact with the flexible wall of the vacuum container.

TABLE 2

Vacuum time for killing old house borer beetle larvae (*hylotrupes bajulus*)

| Initial moisture content (MC), and wood type | Time required for killing larvae | Percentage weight loss of larvae at final measurement |
|---|---|---|
| 7% MC Yellow poplar | 10 hours | 33% |
| 12% MC Yellow pine | 29-48 hours | 36-52% |
| 23% MC Yellow pine | 48-53 hours | 29-40% |
| 70% MC Red oak | Larvae alive after 120 hours | 6% |

In the experimental results in the table above, the time required for killing larvae is given as a range because the exact time of death of the larvae could not be determined with precision. This is because the larvae were unobservable while in the vacuum container, and the vacuum container had to be opened periodically to check the status of the larvae. The time range indicated is the range given by the last time the larvae were observed alive, and the first time they were observed dead.

Significantly, the old house borer larvae survived over 120 hours of exposure to vacuum in red oak containing 70% moisture. Despite the absence of oxygen during this time (oxygen is readily removed by the vacuum pump and displaced by evaporating water), the larvae survived. The larvae were not significantly dehydrated even after 120 hours. The survival of the larvae in this experiment proves that the larvae are killed not by oxygen deprivation, but rather by dehydration. The high moisture content of the wood enabled the larvae to resist dehydration. For this reason, it is preferable in the invention for the wood to have an initial moisture content of less than 50%, more preferably less than 25%, by weight. Insects are more reliably and rapidly killed when the wood has low initial moisture content.

However, it is noted that the old house borer insect is a dry-wood infesting insect and is adapted for living only in dry wood (e.g. typically having less than 20 or 25% moisture content). The old house borer is generally never found in green wood having a moisture content above about 30%. Hence, the above-described experiment with the old house borer in 70% moisture content wood is a situation (a dry-wood insect living in wet wood) that will never be found naturally, and represents the most difficult challenge for vacuum dehydration insect control.

Of particular concern to regulatory agencies are invasive species adapted for living in wet wood (e.g. with moisture content in the range of about 35-80%). Wet wood insects typically attack living trees and therefore pose a threat to forests. Insects adapted to living in wet wood are highly susceptible to dehydration and tend to be easily killed by the present vacuum dehydration method, even when present in wood with a high moisture content. Wet wood insects are not well adapted to obtaining moisture from wet wood, or resisting the dehydrating effect of vacuum exposure.

Dry wood adapted insects (e.g. the old house borer) in dry wood (with less than 25% moisture content) and wet wood adapted insects (e.g. the asian long horned beetle and emerald ash borer) in wet wood (e.g. with greater than 50% moisture content) are generally equally susceptible to vacuum dehydration. In both situations, the insects will typically be destroyed by less than 48 hours of vacuum exposure.

However, there may be situations where a dry wood insect is found in wood with a relatively high moisture content. In this case, the insect will be more difficult to destroy. Killing the insect may require prior drying of the wood (e.g. to reduce moisture content to below 25%, for example), higher temperatures during vacuum exposure, or extended duration vacuum exposure.

Alternatively, if wood with high initial moisture content is used, then the wood and insects can be heated above ambient temperatures to simultaneously dehydrate the wood and kill the insects. More rapid dehydration of the wood will result in more rapid and reliable killing of the insects.

Figure 2:
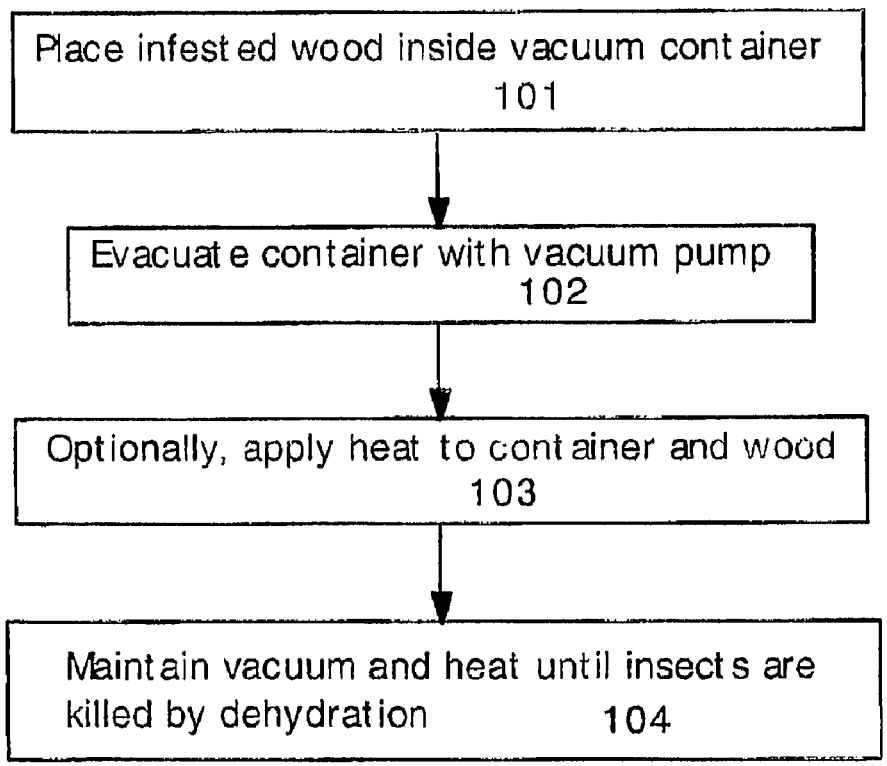
FIG. 2 shows a flow chart of the method of the present invention.

FIG. 2 shows a flow chart of the method of the present invention. In step 101, wood is placed in the vacuum container. The wood can be hardwood or softwood or any other kind of wood. The wood can be cut into square lumber, or rough cut logs. The wood can be wet or dry, but the insects will be more quickly and reliably killed if the wood is at least partially dried.

In step 102, the container is evacuated, and walls of the container press against the wood due to external atmospheric pressure. Contact between the wood and container walls facilitates heat transfer to the wood as moisture evaporates. The temperature of the wood and insects is maintained at ambient or above.

In step 103, heat is applied to the container and wood. Heat can be applied by contacting the container to a heat source, or submerging the container in a heated bath (e.g. comprising water or oil). Alternatively, the container and wood can simply be in contact with air at an ambient temperature. Also, sunlight can be used to heat the container and wood.

In step 104, the vacuum and, preferably, temperature are maintained until insects inside the wood are killed by dehydration. The time required to kill the insect pests in the wood depends on the insect species, wood moisture content, temperature and vacuum pressure. For resistant insect species (e.g., such as the old house borer beetle) in a high moisture content wood, vacuum times exceeding 100 hours, in addition to elevated temperature (e.g. above 35 degrees Celsius) may be necessary. More typically, in dry or partially dry wood, insect pests can be reliably eliminated in about 36-60 hours. In some situations, insects can be reliably killed in 12 hours or less (e.g. an easily dehydrated insect species in dry wood and at elevated temperature).

Optionally, in another aspect of the present invention, desiccant material is added to the container with the wood. The desiccant material can be calcium sulfate, clay, silica, calcium chloride or other desiccant materials that absorb water vapor. The desiccant material can be added as a powder and distributed on the wood, or can be added as removable blocks or bags of material. The desiccant material can be interleaved with the wood to maximize exposure of the wood to the desiccant. The desiccant material will tend to increase the rate of insect dehydration. Preferably, the desiccant material can be replaced or recycled with each batch of processed wood.

Figure 3:
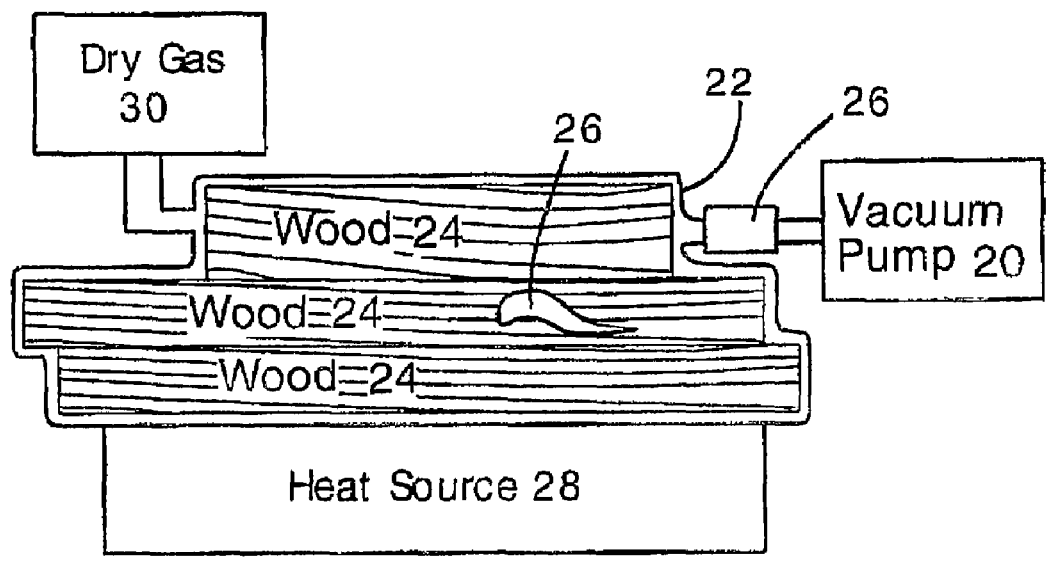
FIG. 3 shows an apparatus for flowing dry gas into the vacuum container to increase the rate of insect dehydration.

FIG. 3 illustrates another aspect of the present invention in which dry gas 30 (e.g. dry air, dry nitrogen, or dry carbon dioxide) is flowed into the vacuum container. The dry gas will tend to increase the rate of water vapor removal, and therefore increase the rate of insect dehydration. The dry gas 30 can be flowed into the vacuum container while the vacuum pump is operating, or can be flowed in during periods while the vacuum pump is off. The dry gas can be flowed continuously or intermittently. The dry gas 30 will tend to decrease the amount of time required to dehydrate and kill insect pests in the wood 24. The dry gas can have a relative humidity of less than 5%, 10% or 20%, for example. Most generally, the dry gas should have a relative humidity less than the relative humidity of the gas within the vacuum chamber.

Figure 4:
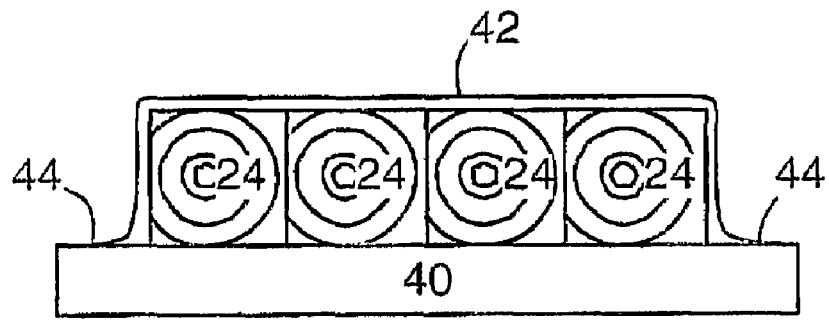
FIG. 4 shows an alternative vacuum container for use with the present invention. The vacuum container has a rigid plate.

In another aspect of the present invention illustrated in FIG. 4, the wood is disposed within a vacuum container having a rigid plate 40. A flexible sheet 42 (e.g. comprising rubber, polyvinyl chloride (PVC), mylar or other impermeable, flexible plastic material) covers the wood 24 and is sealed around the edges 44. The vacuum pump 20 and heat source 28 are not shown. The rigid plate 40 is preferably made of a thermally conductive, impermeable material such as steel or aluminum. In operation, the flexible sheet presses the wood against the rigid plate 40. The rigid plate tends to improve heat conduction into the wood 24. This aspect of the present invention demonstrates that the vacuum container is not necessarily a flexible bag. The vacuum container of the present invention can have a single flexible wall.

Preferably, the wood 24 is oriented within the vacuum container so that a surface cut across wood fibers (e.g. surface cut perpendicular to the wood fibers) is disposed adjacent to where vacuum is applied. In other words, the wood is disposed so that the vacuum port is adjacent to the cut wood fibers. Orienting the wood in this way facilitates dehydration of insects within the wood, because wood typically has a much greater (e.g. 10,000-25,000 times greater) permeability in the direction of the wood fibers. However, it is noted that the present invention includes embodiments where the wood has any orientation with respect to the vacuum port.

It is within the scope of the present invention and appended claims for the wood to be 'heated' simply by placing the vacuum container and wood in an environment at room temperature. For example, the vacuum container and wood can be located in a warehouse, building or outside at a temperature of 15-30 degrees Celsius. The surrounding air will tend to heat the wood by conduction through the vacuum container (e.g. flexible wall), and thereby maintain the temperature of the wood and reasonably high rate of dehydration of the insect pests.

Also, it is noted that the present vacuum treatment method can be used at or below freezing temperatures (0 degrees Celsius). Often, lumber cut and stored in the wintertime is frozen (and possibly covered with ice) and must be treated to destroy insect pests. The present invention is applicable in such situations because insects can be dehydrated even at freezing temperatures and even if ice is present on the wood. The time required for adequate dehydration is higher in freezing temperatures, but the present method is reliable for controlling insects provided that the vacuum is applied for a sufficiently long period of time.

It will be clear to one skilled in the art that the above embodiment may be altered in many ways without departing from the scope of the invention. Accordingly, the scope of the invention should be determined by the following claims and their legal equivalents.

What is claimed is:

1. A method for killing insect pests in wood, comprising the steps of:
   a) measuring an initial moisture content of wood containing insect pests;
   b) disposing said wood in a vacuum-tight container having a flexible wall;
   c) evacuating the container such that the flexible wall presses against the wood; and
   d) performing step c) until the insect pests in the wood are killed or lose at least 25% of their body weight by dehydration, wherein a duration of performing said evacuating step is based on said initial moisture content measured in said measuring step.

2. The method of claim 1 wherein said performing step is performed until the insect pests lose at least 30% of their body weight by dehydration.

3. The method of claim 1 further comprising the step of heating the wood by conducting heat through the flexible wall.

4. The method of claim 3, wherein the wood is heated by thermal contact with a heat source having a temperature in the range of 10-30° Celsius.

5. The method of claim 3 wherein the wood is heated by thermal contact with a heat source having a temperature in the range of 30-55° Celsius.

6. The method of claim 3 wherein the wood is heated by exposing the container to sunlight.

7. The method of claim 1 further comprising the step of disposing a desiccant material inside the vacuum-tight container.

8. The method of claim 1 further comprising the step of flowing dry gas into the vacuum-tight container.

* * * * *